US009366609B2

(12) United States Patent
Kataoka (10) Patent No.: US 9,366,609 B2
(45) Date of Patent: Jun. 14, 2016

(54) HARDNESS TESTER AND METHOD FOR HARDNESS TEST (71) Applicant: MITUTOYO CORPORATION, Kanagawa (JP)

(72) Inventor: Masanobu Kataoka, Miyazaki (JP)

(73) Assignee: MITUTOYO CORPORATION, Kanagawa (JP)

( * ) Notice: Subject to any disclaimer, the term of this patent is extended or adjusted under 35 U.S.C. 154(b) by 533 days.

(21) Appl. No.: 14/024,235

(22) Filed: Sep. 11, 2013

(65) Prior Publication Data
US 2014/0078299 A1    Mar. 20, 2014

(30) Foreign Application Priority Data

Sep. 19, 2012  (JP) .................................. 2012-205678

(51) Int. Cl.
*G01N 3/42* (2006.01)
*G01N 3/40* (2006.01)

(52) U.S. Cl.
CPC .. *G01N 3/42* (2013.01); *G01N 3/40* (2013.01); *G01N 2203/0076* (2013.01); *G01N 2203/0082* (2013.01); *G01N 2203/0094* (2013.01); *G01N 2203/0647* (2013.01)

(58) Field of Classification Search
CPC ... G01N 3/40; G01N 3/42; G01N 2203/0076; G01N 2203/0078
See application file for complete search history.

(56) References Cited

U.S. PATENT DOCUMENTS

| 4,255,966 | A | * | 3/1981 | Batie | G01B 11/024 73/81 |
| 4,463,600 | A | * | 8/1984 | Hobbs | G01B 11/285 356/626 |
| 4,653,106 | A | * | 3/1987 | Yamatsuta | G01B 11/024 348/86 |
| 5,067,346 | A | * | 11/1991 | Field | G01N 3/42 73/81 |
| 6,026,677 | A | * | 2/2000 | Bonin | B82Y 35/00 361/283.2 |
| 7,149,634 | B2 | * | 12/2006 | Ma | G01N 3/42 702/41 |
| 8,578,284 | B2 | | 11/2013 | Takemura et al. | |
| 2013/0047712 | A1 | | 2/2013 | Ariga et al. | |
| 2013/0174653 | A1 | | 7/2013 | Sawa | |

FOREIGN PATENT DOCUMENTS

JP          2011-220790 A    11/2011

* cited by examiner

*Primary Examiner* — Hezron E Williams
*Assistant Examiner* — David Z Huang
(74) *Attorney, Agent, or Firm* — Greenblum & Bernstein, P.L.C.

(57) ABSTRACT

Provided is a hardness tester and method including an indentation former creating an indentation in a sample surface with an indenter; a first area calculator calculating an area of the indentation during application of pressure, the indentation being formed in the sample surface while the indenter is pressed against the sample; an image capture controller controlling a CCD camera to obtain image data of the sample surface; a second area calculator calculating the area of the indentation remaining in the sample surface based on the obtained image data; an elasticity index calculator calculating an elasticity index of the sample based on the area of the indentation during application of pressure and the area of the indentation calculated by the second area calculator; and a hardness value calculator calculating a hardness value of the sample based on the indentation remaining in the sample surface.

4 Claims, 6 Drawing Sheets

Fig. 7 ized by the length of the diagonal lines of the indentation that remains after the indenter has been withdrawn from the sample. Therefore, the same hardness value may be measured even when samples have different elasticity, for example. The conventional hardness testers have thus been unable to distinguish the elasticity of a sample.

SUMMARY OF THE INVENTION

The present invention provides a hardness tester and a method for a hardness test that enable differences in elasticity between samples to be distinguished.

One aspect of the present invention is a hardness tester measuring hardness of a sample placed on a sample stage by loading a predetermined test force on the sample with an indenter to form an indentation in a surface of the sample, then measuring dimensions of the indentation. The hardness tester includes an indentation former, a first area calculator, an image capture controller, a second area calculator, an elasticity index calculator, and a hardness value calculator. The indentation former creates the indentation in the surface of the sample by pressing the indenter against the surface of the sample. The first area calculator calculates an area of the indentation during application of pressure, the indentation being formed in the surface of the sample when the indenter is pressed against the sample surface by the indentation former. The image capture controller controls an image capturer to capture an image of the sample surface and obtain image data of the sample surface. The second area calculator calculates the area of the indentation that remains in the sample surface based on the image data obtained by the image capturer after the indenter has retreated from the sample surface. The elasticity index calculator calculates an elasticity index of the sample based on the area of the indentation during application of pressure, calculated by the first area calculator, and the area of the indentation calculated by the second area calculator. The hardness value calculator calculates a hardness value of the sample based on the indentation that remains in the sample surface.

Another aspect of the present invention is the hardness tester further including a display controller displaying on a display an image of the sample surface based on the image data obtained by the image capturer. The display controller displays, on the display, the elasticity index of the sample calculated by the elasticity index calculator and the hardness value of the sample calculated by the hardness value calculator.

Another aspect of the present invention is the hardness tester in which, based on the area of the indentation during application of pressure calculated by the first area calculator, the display controller displays a shape of the indentation during application of pressure when the indenter is pressed against the sample, the shape being displayed overlaid on an indentation in an image of the sample surface.

Another aspect of the present invention is a method for a hardness test for a hardness tester measuring hardness of a sample placed on a sample stage by loading a predetermined test force on the sample with an indenter to form an indentation in a surface of the sample, then measuring dimensions of the indentation. The hardness testing method includes indentation forming, first area calculation, image capture control, second area calculation, elasticity index calculation, and hardness value calculation. The indentation forming creates the indentation in the sample surface by pressing the indenter against the sample surface. The first area calculation calculates an area of the indentation during application of pressure, the indentation being formed in the sample surface when the indenter is pressed against the sample surface during the indentation forming. The image capture control controls an image capturer to capture an image of the sample surface and obtain image data of the sample surface. The second area calculation calculates the area of the indentation that remains in the sample surface based on the image data obtained by the image capturer after the indenter has retreated from the sample surface. The elasticity index calculation calculates an elasticity index of the sample based on the area of the indentation during application of pressure, calculated during the first area calculation, and the area of the indentation calculated during the second area calculation. The hardness value calculation calculates a hardness value of the sample based on the indentation that remains in the sample surface.

The present invention calculates not only a hardness value of a sample, but also enables an elasticity index of the sample to be calculated, thus enabling differences in elasticity between samples to be distinguished.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, an embodiment of the present invention is described in detail with reference to the drawings. Moreover, in the following description, an X direction is a left-right direction, a Y direction is a front-back direction, and a Z direction is an up-down direction in FIG. 1. In addition, an X-Y plane is a horizontal plane.

A hardness tester 100 is a Vickers hardness tester, for example, that includes an indenter 14a (see FIG. 3) having a square planar shape. As shown in FIGS. 1 to 4, the hardness tester 100 is configured to include a hardness tester main body 10, a controller 6, an operator 7, a monitor 8, and an indenter column displacement detector 9.

Figure 2:
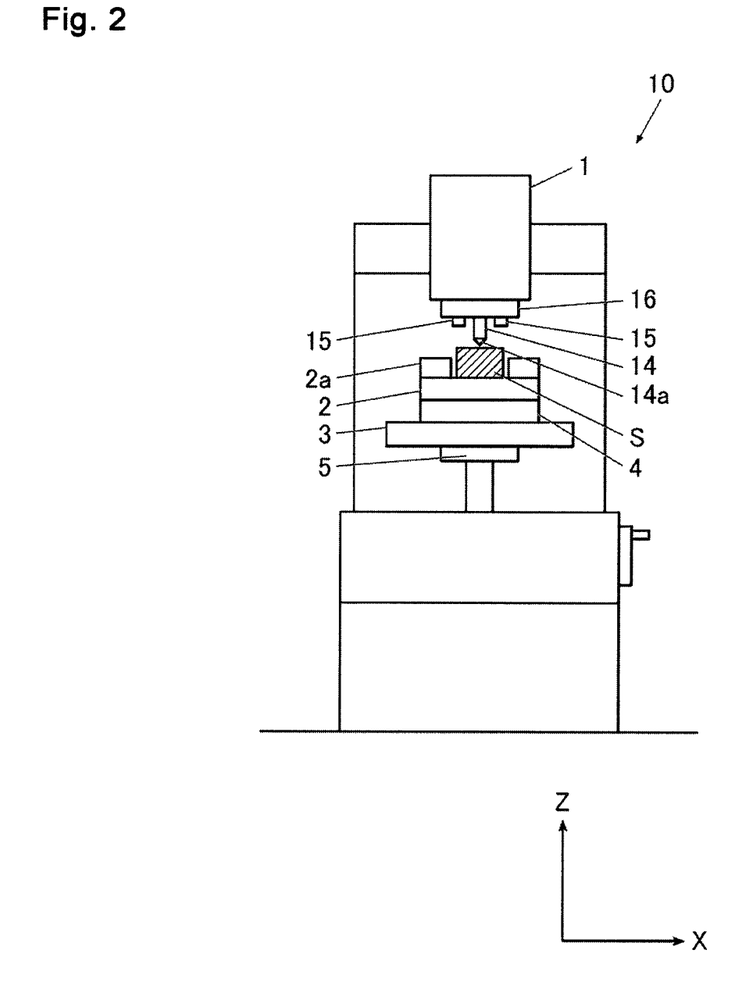
FIG. 2 is a schematic view illustrating a hardness tester main body of the hardness tester according to the present invention.

As shown in FIG. 2, the tester main body 10 includes a hardness measurer 1 measuring hardness of a sample S; a sample stage 2 on which the sample S is placed; an XY stage 3 displacing the sample stage 2; an AF stage 4 for focusing on a surface of the sample S; and an elevator mechanism 5 raising and lowering the sample stage 2 (the XY stage 3 and the AF stage 4).

Figure 3:
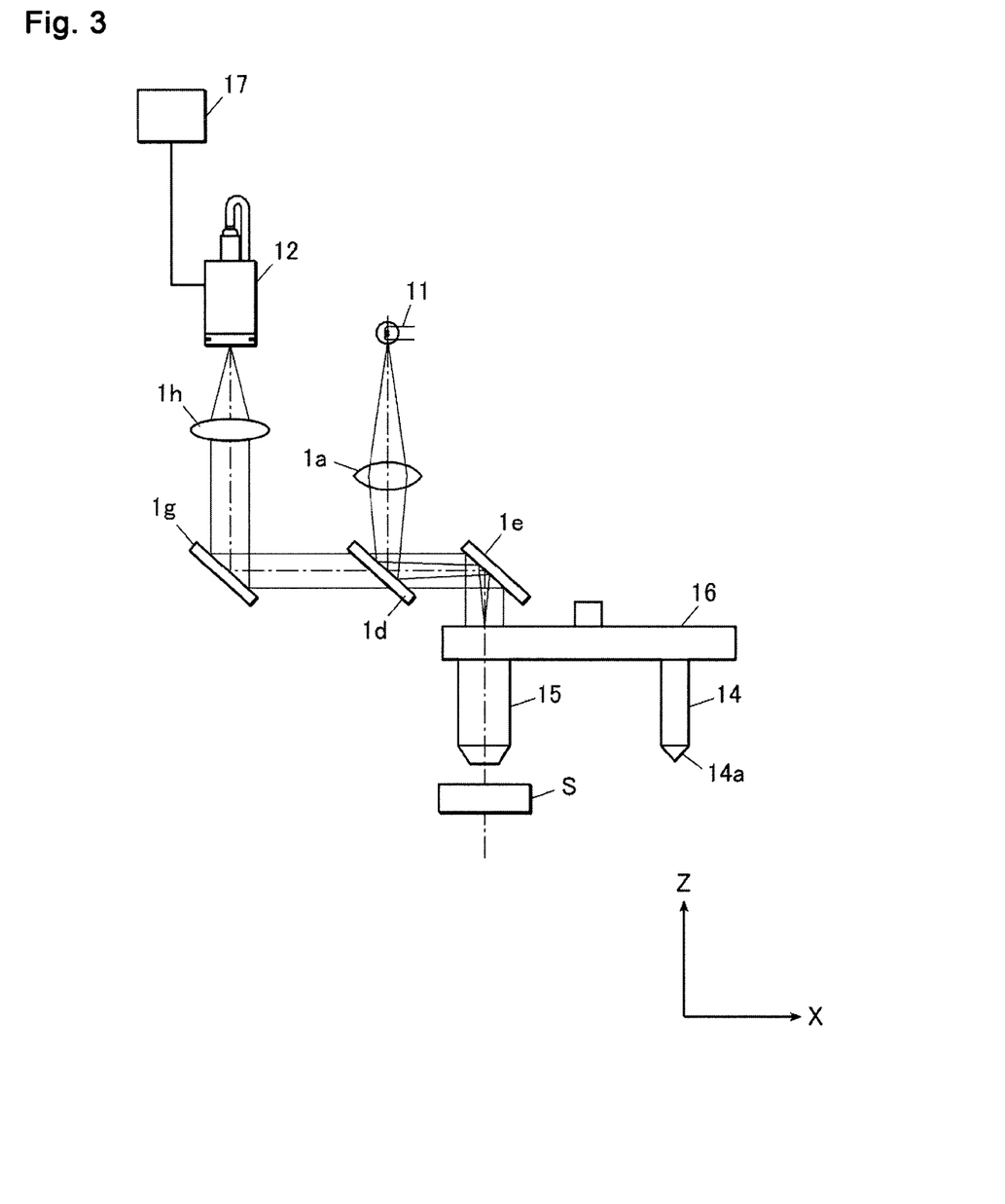
FIG. 3 is a schematic view illustrating a hardness measurer of the hardness tester according to the present invention.

As shown in FIG. 3, the hardness measurer 1 is configured with an illuminating device 11 illuminating the surface of the sample S; a CCD camera 12 capturing an image of the surface of the sample S; and a turret 16. The turret 16 includes an indenter column 14, which includes the indenter 14a, and a field lens 15. The turret 16 is capable of switching between the indenter column 14 and the field lens 15 by rotating.

The illuminating device 11 shines a light to illuminate the surface of the sample S. The light shone by the illuminating device 11 reaches the surface of the sample S via a lens 1a, a half mirror 1d, a mirror 1e, and the field lens 15.

Based on reflected light input from the surface of the sample S via the field lens 15, the mirror 1e, the half mirror 1d, a mirror 1g, and a lens 1h, the CCD camera 12 obtains image data by capturing an image of the surface of the sample S as well as the indentation formed in the surface of the sample S by the indenter 14a. The CCD camera 12 then outputs the image data to the controller 6 via a frame grabber 17, which is capable of simultaneously accumulating and storing a plurality of frames of image data. Thus, the CCD camera 12 is an image capturer in the present invention.

The indenter column 14 is displaced toward the sample S placed on the sample stage 2 by a load mechanism (not shown in the drawings), which is driven in response to a control signal output by the controller 6. The indenter 14a, provided on a forefront end of the indenter column 14, is pressed against the surface of the sample S with a predetermined test force. The present embodiment uses a quadrangular pyramidal Vickers indenter (with opposing angles of) 136±0.5°.

The field lens 15 is a collective lens, each lens being configured with a different magnification. A plurality of the field lenses 15 are retained on the bottom surface of the turret 16 and are disposed above the sample S by rotating the turret 16. Thereby, the light shone by the illuminating device 11 uniformly illuminates the surface of the sample S.

The turret 16 is configured so as to enable the indenter column 14 and the plurality of field lenses 15 to be attached to a bottom surface thereof. The turret 16 is also configured to be capable of disposing any one of the indenter column 14 and the plurality of field lenses 15 above the sample S by rotating the turret 16 around a Z-axis direction. Specifically, the indentation can be formed in the surface of the sample S by disposing the indenter column 14 above the sample S, and the formed indentation can be observed by disposing the field lenses 15 above the sample S.

The sample S is placed on an upper surface of the sample stage 2 and is fixed in place with a sample holder 2a. The XY stage 3 is driven by a drive mechanism (not shown in the drawings) driven in response to the control signal output by the controller 6. The XY stage 3 then displaces the sample stage 2 in a direction (X and Y directions) perpendicular to the displacement direction (Z direction) of the indenter 14a. The AF stage 4 is driven in response to the control signal output by the controller 6. The AF stage 4 then minutely raises and lowers the sample stage 2 based on the image data captured by the CCD camera 12 to focus on the surface of the sample S. The elevator mechanism 5 is driven in response to the control signal output by the controller 6. The elevator mechanism 5 then changes a relative distance between the sample stage 2 and the field lens 15 by displacing the sample stage 2 (the XY stage 3 and the AF stage 4) in the Z direction.

Figure 1:
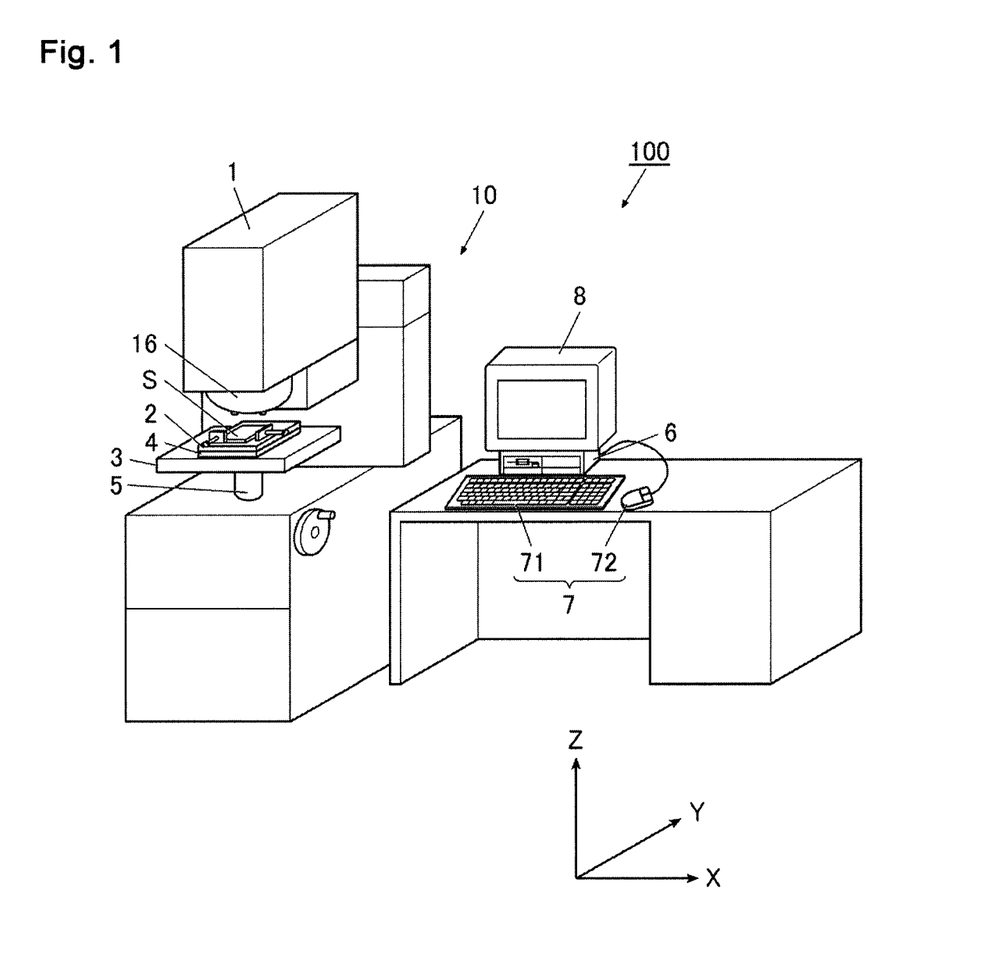
FIG. 1 is a perspective view illustrating an overall configuration of a hardness tester according to the present invention.

The operator 7 is configured with a keyboard 71 and a mouse 72. The operator 7 executes an operation input by the user during a hardness test. In addition, when a predetermined input operation is performed by the operator 7, a predetermined operation signal corresponding to the input operation is output to the controller 6. Specifically, the operator 7 enables the user to select conditions determining a focus position of the indentation using the keyboard 71 and the mouse 72. The operator 7 also enables to the user to designate a range of displacement (a range of relative distance between the sample stage 2 and the field lens 15) of the sample stage 2 (the elevator mechanism 5 and the AF stage 4). In addition, the operator 7 enables the user to input a test condition value when carrying out the hardness test with the hardness tester 100. The input test condition value is transmitted to the controller 6. Herein, the test condition value is a value such as a material of the sample S, a test force (N) loaded on the sample S by the indenter 14*a*, or a magnification power of the field lens 15, for example. In addition, the operator 7 enables the user to select one of a manual mode, in which the focus position of the indentation is manually determined, and an automatic mode, in which the determination is made automatically.

The monitor 8 is configured with a display device such as an LCD, for example. The monitor 8 displays, for example, settings of the hardness test input on the operator 7, results of the hardness test, and an image of the surface of the sample S and the indentation formed in the surface of the sample S captured by the CCD camera 12. Thus, the monitor 8 is a display in the present invention.

The indenter column displacement detector 9 includes, for example, a scale provided to the indenter column 14 and carved with calibration marks at predetermined intervals, and a linear encoder optically reading the calibration marks on the scale. The indenter column displacement detector 9 detects an amount of displacement when the indenter column 14 forms the indentation in the sample S (i.e., an amount of ingress of the indenter 14*a* being pressed into the sample S), then outputs an indenter column displacement signal to the controller 6 based on the detected amount of displacement.

Figure 4:
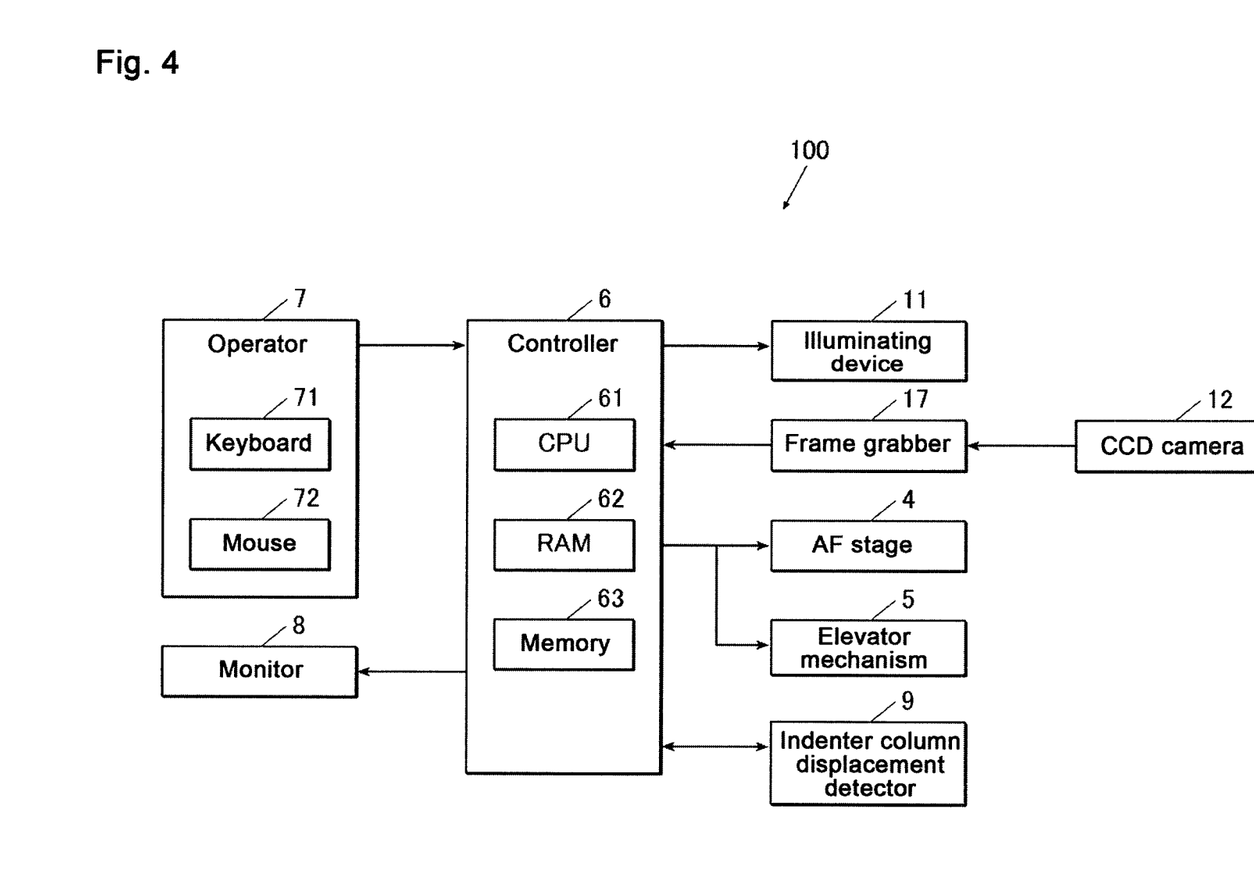
FIG. 4 is a block diagram illustrating a control structure of the hardness tester according to the present invention.

As shown in FIG. 4, the controller 6 is configured to include a CPU (Central Processing Unit) 61, a RAM (Random Access Memory) 62, and a memory 63. The controller 6 performs operation control of performance of a predetermined hardness test by executing a predetermined program stored in the memory 63.

The CPU 61 retrieves a processing program stored in the memory 63, then opens and executes the processing program in the RAM 62. The CPU 61 thus performs overall control of the hardness tester 100.

The RAM 62 opens the processing program executed by the CPU 61 in a program storage region within the RAM 62 and stores in a data storage region input data and processing results generated during execution of the processing program, and the like.

The memory 63 includes, for example, a recording medium (not shown in the drawings) storing a program, data, and the like. The recording medium is configured with a semiconductor memory, for example. In addition, the memory 63 stores various kinds of data, various kinds of processing programs, and data processed by running the programs that allow the CPU 61 to perform overall control of the hardness tester 100.

Figure 5:
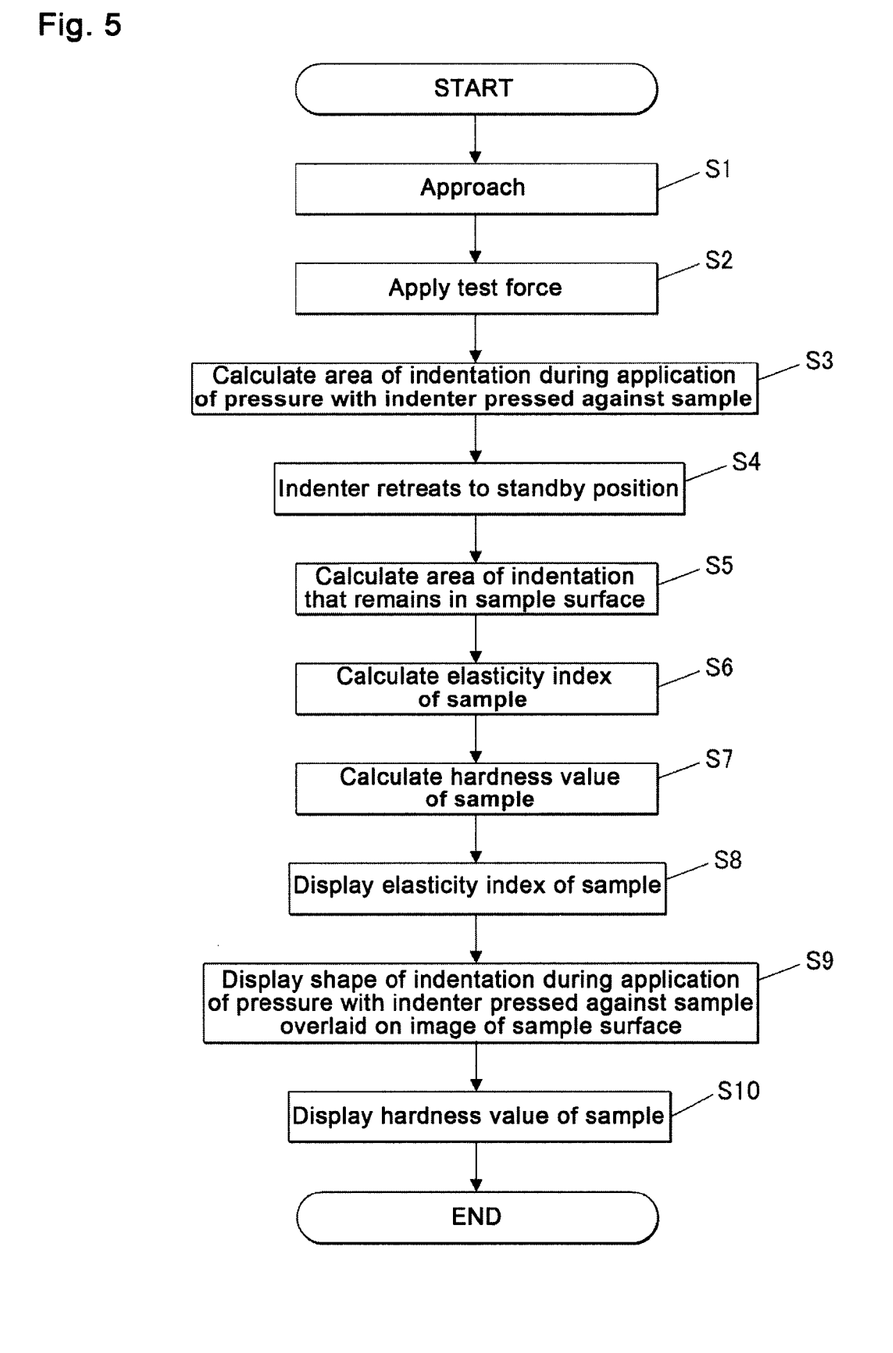
FIG. 5 is a flow chart illustrating operations of the hardness tester according to the present invention.

Next, operations of the hardness tester 100 according to the present embodiment are described with reference to the flow chart of FIG. 5. First, a process is performed to advance the indenter 14*a* toward the sample S (step S1). Specifically, when the field lens 15 has been positioned above the sample S by rotating the turret 16, the CPU 61 displaces the XY stage 3 so as to position a predetermined area on the surface of the sample S directly beneath the field lens 15. Next, the CPU 61 raises and lowers the AF stage 4 to perform automatic focusing on the surface of the sample S based on the image data obtained by the CCD camera 12 on the hardness measurer 1. Then, when the indenter column 14 has been positioned above the sample S by rotating the turret 16, the CPU 61 displaces the indenter column 14 until the indenter 14*a*, provided to the forefront end of the indenter column 14, touches the surface of the sample S.

Next, a process is performed to apply a test force to the sample S (step S2: indentation forming). Specifically, the CPU 61 gradually applies force to press the indenter 14*a* against the surface of the sample S until reaching the predetermined test force, thus forming the indentation during application of pressure on the surface of the sample S. Then, the CPU 61 holds the indenter 14*a* in a state of pressing against the sample S with the predetermined test force.

Figure 6A:
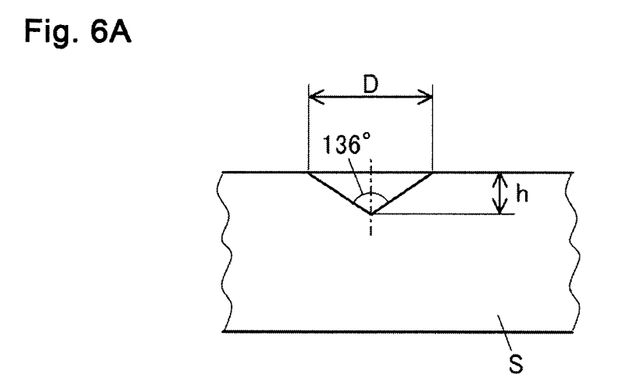
FIGS. 6A and 6B illustrate a method for calculating an area of an indentation during application of pressure when an indenter is pressed against the sample with a predetermined test force.
Figure 6B:
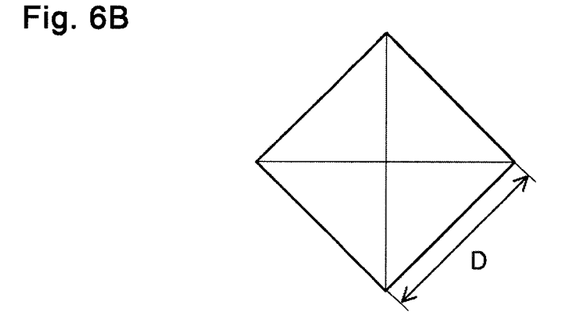

Next, an area of the indentation during application of pressure in step S2 is calculated while the indenter 14*a* is pressed against the sample S with the predetermined test force (step S3: first area calculation). Specifically, the CPU 61 calculates a length D of one side of the indentation during application of pressure based on an amount of ingress h of the indenter 14*a* into the sample S as detected by the indenter column displacement detector 9 (see FIGS. 6A and 6B). Herein, the length D of one side of the indentation during application of pressure can be calculated using formula 2.

$$D = \tan(136°/2) \times h \times 2 \quad \text{[Formula 2]}$$

Then, in view of a square planar shape of the indentation during application of pressure formed by the Vickers indenter 14*a*, the CPU 61 squares the calculated length D of one side of the indentation during application of pressure to calculate an area M1 (=D×D) of the indentation during application of pressure. Specifically, the CPU 61 is the first area calculator of the present invention calculating the area M1 of the indentation during application of pressure formed in the surface of the sample S while the indenter 14*a* is pressed against the surface of the sample S.

Next, a process is performed to withdraw the indenter 14*a*, which is pressed against the sample S, to a predetermined standby position (step S4). Specifically, the CPU 61 gradually pulls the indenter column 14 up in the Z direction from where the indenter 14*a* was pressed against the surface of the sample S, withdrawing the indenter column 14 to the predetermined standby position. The CPU 61 then holds the indenter column 14 in the standby position. Thereby, the indentation is formed in the surface of the sample S. Specifically, the CPU 61 is the indentation former of the present invention creating the indentation in the surface of the sample S by pressing the indenter 14*a* against the surface of the sample S.

Next, the area of the indentation that remains in the surface of the sample S after the indenter 14*a* has been withdrawn in step S4 is calculated (step S5: image capture control, second area calculation). Specifically, when the field lens 15 has been positioned above the sample S by rotating the turret 16, the CPU 61 captures an image of the surface of the sample S with the CCD camera 12 to obtain image data. Then, the CPU 61 analyzes the obtained image data to measure a length of diagonal lines in the indentation formed in the surface of the sample S, then calculates an area M2 of the indentation based on the measured length of the diagonal lines. Specifically, the CPU 61 is the image capture controller of the present invention controlling the CCD camera 12 to capture an image of the surface of the sample S and obtain image data of the surface of the sample S. In addition, the CPU 61 is the second area calculator of the present invention calculating the area M2 of the indentation that remains in the surface of the sample S after the indenter 14*a* has retreated from the surface of the sample S, the CPU 61 calculating the area M2 based on the image data obtained by the CCD camera 12.

Next, an elasticity index of the sample S is calculated (step S6: elasticity index calculation). Specifically, the CPU 61 calculates an elasticity index A (=M2/M1) of the sample S by dividing the area M2 of the indentation remaining in the surface of the sample S, calculated in step S5, by the area M1 of the indentation during application of pressure calculated in step S3 while the indenter 14*a* is pressed against the sample S. In other words, the CPU 61 is the elasticity index calculator of the present invention calculating the elasticity index A of the sample S based on the area M1 of the indentation during application of pressure, calculated in step S3 while the indenter 14a is pressed against the sample S, and the area M2 of the indentation remaining in the surface of the sample S, calculated in step S5.

Next, a hardness value of the sample S is calculated (step S7: hardness value calculation). Specifically, the CPU 61 calculates a hardness value HV (=0.1891 F/d$^2$) of the sample S based on the length of the diagonal lines of the indentation measured by analysis of the image data in step S5. In other words, the CPU 61 is the hardness value calculator of the present invention calculating the hardness value HV of the sample S based on the indentation remaining in the surface of the sample S.

Next, the elasticity index A of the sample S is displayed on the monitor 8 (step S8). Specifically, the CPU 61 displays on the monitor 8 the elasticity index A of the sample S, calculated in step S6.

Figure 7:
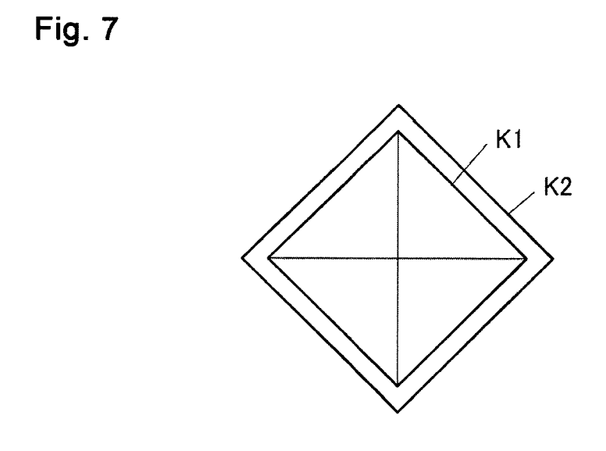
FIG. 7 is an exemplary diagram illustrating display of a shape of the indentation during application of pressure when the indenter is pressed against the sample with the predetermined test force, the shape being displayed overlaid on an indentation in an image of the sample surface.

Next, the shape of the indentation during application of pressure while the indenter 14a is pressed against the sample S with the predetermined test force is displayed on the monitor 8 overlaid on an indentation in an image of the surface of the sample S (step S9). Specifically, as shown in FIG. 7, based on the image data obtained in step S5, the CPU 61 displays on the monitor 8 the image of the surface of the sample S, which includes an indentation K1 that remains on the surface of the sample S after the indenter 14a is drawn up. In addition, based on information of the indentation during application of pressure obtained in step S3 (the length D of one side, the area M1, etc.), the CPU 61 displays, overlaid on the image of the surface of the sample S, the shape of an indentation K2 during application of pressure while the indenter 14a is pressed against the sample S with the predetermined test force. Thereby, the user can visually compare the indentation K1 that remains on the surface of the sample S with the indentation K2 during application of pressure while the indenter 14a is pressed against the sample S. The user can therefore readily identify the nature of elastic deformation of the indentation. Specifically, the CPU 61 is the display controller of the present invention displaying the image of the surface of the sample S on the monitor 8 based on the image data obtained by the CCD camera 12 and, based on the area M1 of the indentation during application of pressure, calculated in step S3, the CPU 61 displays the shape of the indentation K2 during application of pressure while the indenter 14a is pressed against the sample S, the shape being displayed overlaid on the indentation K1 on the image of the surface of the sample S.

Next, the hardness value HV of the sample S is displayed on the monitor 8 (step S10). Specifically, the CPU 61 displays on the monitor 8 the hardness value HV of the sample S calculated in step S7.

As described above, the hardness tester 100 according to the present embodiment includes the indentation former (CPU 61) creating the indentation in the surface of the sample S by pressing the indenter 14a against the surface of the sample S; the first area calculator (CPU 61) calculating the area M1 of the indentation during application of pressure, the indentation being formed in the surface of the sample S while the indenter 14a is pressed against the surface of the sample S by the indentation former; the image capture controller (CPU 61) controlling the CCD camera 12 to capture the image of the surface of the sample S and obtain the image data of the surface of the sample S; the second area calculator (CPU 61) calculating the area M2 of the indentation that remains in the surface of the sample S based on the image data obtained by the CCD camera 12 after the indenter 14a has retreated from the surface of the sample S; the elasticity index calculator (CPU 61) calculating the elasticity index A of the sample S based on the area M1 of the indentation during application of pressure, which was calculated by the first area calculator, and the area M2 of the indentation calculated by the second area calculator; and the hardness value calculator (CPU 61) calculating the hardness value HV of the sample S based on the indentation remaining in the surface of the sample S. Therefore, the hardness tester 100 according to the present embodiment can not only calculate the hardness value HV of the sample S, but can also calculate the elasticity index A of the sample S, and thus can distinguish differences in elasticity between samples.

In addition, the hardness tester 100 according to the present embodiment further includes the display controller (CPU 61) displaying on the monitor 8 the image of the surface of the sample S based on the image data obtained by the CCD camera 12. The display controller displays the elasticity index A of the sample S (calculated by the elasticity index calculator) and the hardness value HV of the sample S (calculated by the hardness value calculator) on the monitor 8. Therefore, the use can readily identify the elasticity index A and the hardness value HV of the sample S.

In addition, in the hardness tester 100 according to the present embodiment, based on the area M1 of the indentation during application of pressure calculated by the first area calculator, the display controller displays the shape of the indentation K2 during application of pressure while the indenter 14a is pressed against the sample S, the shape being displayed overlaid on the indentation K1 in the image of the surface of the sample S. Therefore, the user can visually compare the indentation K1 that remains on the surface of the sample S with the indentation K2 during application of pressure while the indenter 14a is pressed against the sample S. The user can thus readily identify the nature of elastic deformation of the indentation.

Above, a concrete description was given based on an embodiment according to the present invention. However, the present invention is not limited to the above-described embodiment and may be modified within a scope not deviating from the substance of the invention.

For example, in the above-described embodiment, after the elasticity index A of the sample S is calculated in step S6 (see FIG. 5), the hardness value HV of the sample S is calculated in step S7. However, the present invention is not limited to this. The process of step S6 and the process of step S7 may be switched in order, for example. In addition, for example, the process of step S7 may be performed immediately before the process of step S10, in which the hardness value HV of the sample S is displayed on the monitor 8. In addition, for example, the elasticity index A of the sample S may be calculated and displayed on the monitor 8 after the hardness value HV of the sample S is calculated and displayed on the monitor 8, or the calculated hardness value HV and elasticity index A may be displayed simultaneously on the monitor 8. In other words, there is no particular order to the calculation of the elasticity index A and the hardness value HV, which can be displayed on the monitor 8 at any time after being calculated.

In the above-described embodiment, by displaying the elasticity index A and the hardness value HV of the sample S on the monitor 8 (refer to steps S8 and S10 in FIG. 5), the user is notified of these values. However, the present invention is not limited to this. For example, a speaker capable of audio output may be provided, and the calculated elasticity index A and hardness value HV of the sample S may be audibly output from the speaker.

In addition, in the above-described embodiment, a Vickers hardness tester was described to exemplify the hardness tester 100. However, the present invention is not limited to this. The present invention may be applied to any hardness tester having an indenter with a known shape. For example, the present invention may also be applied to a Knoop hardness tester having a rhomboid pyramid diamond indenter.

In addition, within a scope not deviating from the substance of the present invention, appropriate modifications may also be made to detailed structures and operations of each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester measuring hardness of a sample placed on a sample stage by loading a predetermined test force on the sample with an indenter to form an indentation in a surface of the sample, then measuring dimensions of the indentation, the hardness tester comprising:
    an indentation former configured to create the indentation in the sample surface by pressing the indenter against the sample surface;
    a first area calculator configured to calculate an area of the indentation during application of pressure, the indentation being formed in the sample surface while the indenter is pressed against the sample surface by the indentation former;
    an image capture controller configured to control an image capturer to capture an image of the sample surface and obtain image data of the sample surface;
    a second area calculator configured to calculate the area of the indentation that remains in the sample surface based on the image data obtained by the image capturer after the indenter has retreated from the sample surface;
    an elasticity index calculator configured to calculate an elasticity index of the sample based on the area of the indentation during application of pressure, calculated by the first area calculator, and the area of the indentation calculated by the second area calculator; and
    a hardness value calculator configured to calculate a hardness value of the sample based on the indentation remaining in the sample surface.

2. The hardness tester according to claim 1 further comprising:
    a display controller configured to display, on a display, an image of the sample surface based on the image data obtained by the image capturer, wherein the display controller is further configured to display, on the display, the elasticity index of the sample calculated by the elasticity index calculator and the hardness value of the sample calculated by the hardness value calculator.

3. The hardness tester according to claim 2, wherein the display controller is configured to display, based on the area of the indentation during application of pressure calculated by the first area calculator, a shape of the indentation during application of pressure while the indenter is pressed against the sample, the shape being displayed overlaid on an indentation in an image of the sample surface.

4. A hardness testing method for a hardness tester measuring hardness of a sample placed on a sample stage by loading a predetermined test force on the sample with an indenter to form an indentation in a surface of the sample, then measuring dimensions of the indentation, the hardness testing method comprising:
    creating the indentation in the sample surface by pressing the indenter against the sample surface;
    calculating an area of the indentation during application of pressure, the indentation being formed in the sample surface when the indenter is pressed against the sample surface during the creating the indentation;
    controlling an image capturer to capture an image of the sample surface and obtain image data of the sample surface;
    calculating the area of the indentation that remains in the sample surface based on the image data obtained by the image capturer after the indenter has retreated from the sample surface;
    calculating an elasticity index of the sample based on the area of the indentation during application of pressure, calculated during the calculating the area of the indentation during application of pressure, and further based on the area of the indentation calculated during the calculating the area of the indentation that remains in the sample surface; and
    calculating a hardness value of the sample based on the indentation that remains in the sample surface.

* * * * *